United States Patent
Kim

(10) Patent No.: US 6,890,174 B2
(45) Date of Patent: May 10, 2005

(54) ANCHOR IMPLANTING DEVICE FOR ORTHODONTICS

(76) Inventor: Joong-han Kim, Seocho 4cha Hyundai Apt. #201-1601, Seocho-4dong, Seocho-ku, Seoul City (KR)

(*) Notice: Subject to any disclaimer, the term of this patent is extended or adjusted under 35 U.S.C. 154(b) by 85 days.

(21) Appl. No.: 10/227,267

(22) Filed: Aug. 26, 2002

(65) Prior Publication Data

US 2003/0044745 A1 Mar. 6, 2003

(30) Foreign Application Priority Data

Aug. 28, 2001 (KR) ......................................... 2001-52054

(51) Int. Cl.[7] .............................. A61C 3/00; A61C 8/00
(52) U.S. Cl. ......................................... 433/18; 433/173
(58) Field of Search ............................. 433/4, 18, 172, 433/173, 174, 175, 176

(56) References Cited

U.S. PATENT DOCUMENTS

| | | | | |
|---|---|---|---|---|
| 2,579,829 A | * | 12/1951 | Joyce | |
| 5,133,662 A | * | 7/1992 | Metcalfe | 433/173 |
| 5,853,291 A | * | 12/1998 | DeVincenzo et al. | 433/176 |
| 5,921,774 A | | 7/1999 | Kanomi et al. | |
| 6,193,509 B1 | * | 2/2001 | DeVincenzo | 433/18 |
| 6,287,118 B1 | * | 9/2001 | Naganuma et al. | 433/176 |
| 6,354,834 B2 | * | 3/2002 | Kanomi et al. | 433/18 |

FOREIGN PATENT DOCUMENTS

DE            3914623          11/1990

* cited by examiner

*Primary Examiner*—Cary E. O'Connor
(74) *Attorney, Agent, or Firm*—Stites & Harbison PLLC; Douglas E. Jackson

(57) ABSTRACT

An anchor implanting device for orthodontics used for implanting an wire supporting anchor supporting a teeth supporting wire which supports a plurality of teeth and correct the teeth, comprises a tooth supporter supportedly enclosing a portion between a pair of neighboring teeth elastically in a transverse direction relative to an array direction of the teeth; a locating projection projected inward in a radial direction from the tooth supporter and positioned between the pair of neighboring teeth and a gum; at least one anchor positioning unit extended from the tooth supporter, positioned on the side of the gum so as to establish an implanting position of the wire supporting anchor. With this configuration, the present invention provides an anchor implanting device for orthodontics, allowing a wire supporting anchor to be implanted on the predetermined position of the gum in an easy manner. Further, by using the anchor implanting device according to the present invention, the time for operating the implantation of the wire supporting anchor is reduced, thereby accomplishing the effect of cost saving.

5 Claims, 8 Drawing Sheets

ANCHOR IMPLANTING DEVICE FOR ORTHODONTICS

BACKGROUND OF INVENTION

1. Field of the Invention

The present invention relates in general to anchor implanting devices for orthodontics, and more particularly, to an anchor implanting devices for orthodontics, used in implanting a wire supporting anchor supporting an orthodontic wire, making orthodontics of one or more teeth by supporting a plurality of teeth together.

2. Description of the Related Art

Generally, when operating orthodontics to treat false occlusion of the teeth, it is very important to control a force produced between moving teeth (mainly, front teeth) to be moved and fixed teeth (mainly, molars) not to be moved, for a better chewing by the molars and a more improved utterance and an aesthetic function by the front teeth.

For example, in the case of making an orthodontics of a projecting tooth or a slant tooth, an orthodontic device comprised of brackets mounted to the teeth and an orthodontic wire connecting the brackets has been used, after a small molar is pulled out, and then a front tooth is moved toward the molar region pulled out.

A reaction toward the molar is applied to the front tooth so as to be moved, due to this orthodontic device. However, a reaction in reverse is generated in the molar region, thereby causing the molar to be moved forward and occupy the position of the tooth pulled out, even though the molar is not to be moved, and therefore, it is problematic because the front teeth cannot be moved as long as desired.

To solve this problem, in the orthodontics an orthodontic device detachably coupled to the teeth has been used, in order to reduce the reaction as mentioned above and provide a sufficient space in which the moving teeth can be moved. However, in the case of adults, it has not been easy to obtain an agreement to mount the detachable orthodontic device to their teeth because it is neither aesthetic nor it is convenient to insert it into and detach it from the teeth.

Recently, small screws have been implanted into alveolar bones of the gum between the roots of the teeth, and the teeth to be made orthodontics and the wire supporting anchor are ligated by means of an elastic material, thereby allowing them to be used as fixtures for fixing them in a secure and continued manner (which is called "mini implant"). Since the wire supporting anchor is implanted between the roots of the teeth, it is not shown to the outside. Also, since the fixing force is strong, the mini implant can exercise its force for the whole day. Thus, this device is advantageous in that the teeth can be moved as soon as possible.

However, since the teeth are covered with the gum and the whole part of the molar region is not seen to the operator, it is not easy to implant a wire supporting anchor correctly between the roots of the teeth so as not to cause damages to the root of the teeth.

Thus, in a conventional implanting device, a small dental mirror has been used to exactly implant the anchor between the roots of the teeth, by the means of a pincette or an anesthetic injection needle, since the exact position of the gum between the teeth can be indicated. Otherwise, the implantation has been operated after ascertaining, by the means of an X-ray, the exact position for implantation of the wire supporting anchor between the roots of the teeth. However, this method has been available only for indicating an external position of the gum, and thus, the direction may be out of joint when actually implanting the wire into the bone. In addition, this method has caused inconvenience in operating the implantation. Therefore, the conventional implanting devices have increased the time and cost for operation of the implantation.

SUMMARY OF THE INVENTION

Accordingly, it is an object of the present invention to provide an anchor implanting device for orthodontics, which allows the wire supporting anchor to be easily implanted to a position of the gum as predetermined.

Another object of the present invention is to provide an anchor implanting device for orthodontics so as to reduce the time of operation for the implantation of the wire supporting anchor and save the operating cost.

The foregoing and other objects of the present invention are achieved by providing an anchor implanting device for orthodontics used for implanting an wire supporting anchor supporting a teeth supporting wire which supports a plurality of teeth and correct the teeth, comprising a tooth supporter supportedly enclosing a portion between a pair of neighboring teeth elastically in a transe verse direction relative to an array direction of the teeth; a locating projection projected inward in a radial direction from the tooth supporter and positioned between the pair of neighboring teeth and a gum; at least one anchor positioning unit extended from the tooth supporter, positioned on the side of the gum so as to establish an implanting position of the wire supporting anchor.

Preferably, the anchor positioning unit takes the form of a fork, being formed with an anchor inserting groove. Further, the anchor positioning unit has a surface of curvature corresponding to the side of the gum.

Preferably, the anchor implanting device further comprises a shaft rotatably supporting the tooth supporters in a pair, wherein the anchor positioning unit is connected to each of the tooth supporters in a pair.

Further, the anchor implanting device further comprises a pair of handle parts respectively connected to the pair of tooth supporters, allowing the tooth supporters to approach to and separate from each other relative to the shaft.

Preferably, an elastic spring is mounted on the shaft, elastically moving the pair of tooth supporters to be close to each other.

Preferably, the anchor positioning unit is detachably coupled to the tooth supporter.

BRIEF DESCRIPTION OF THE DRAWINGS

These and other objects and advantages of the present invention will become apparent and more readily appreciated from the following description of the embodiments, taken in conjunction with the accompanying drawings of which.

DETAILED DESCRIPTION OF THE PREFERRED EMBODIMENTS

Figure 1:
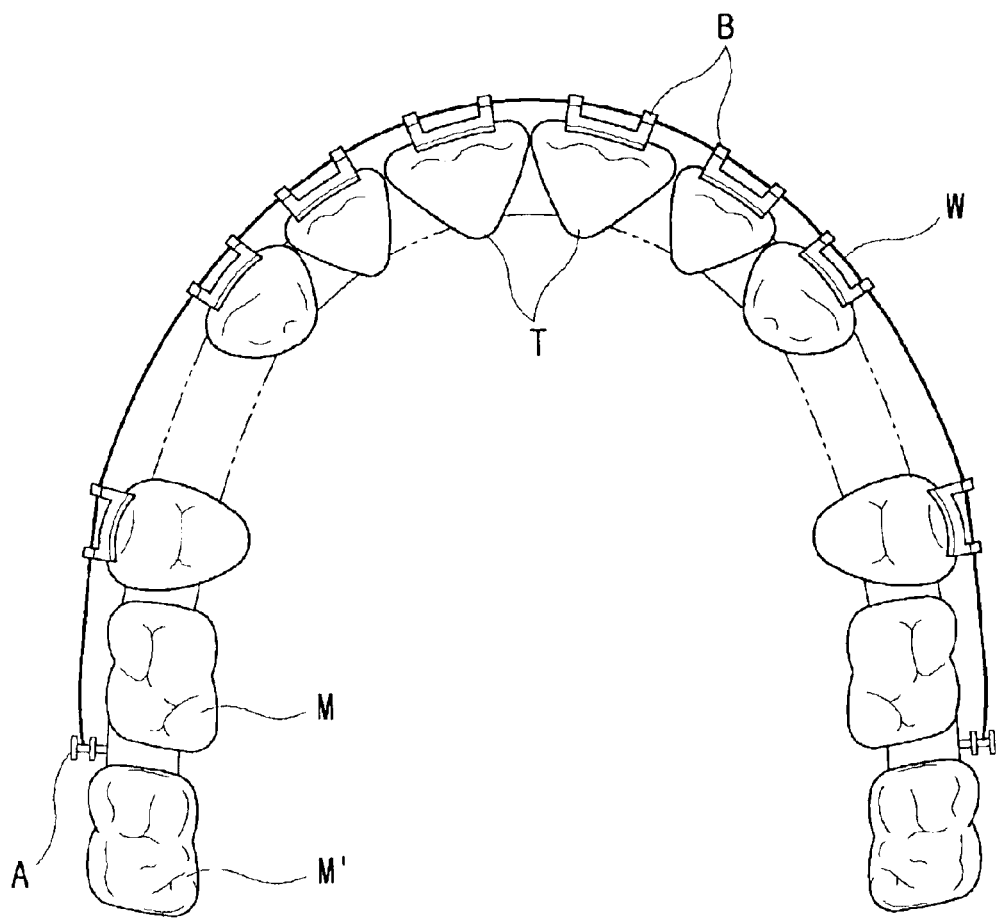
FIG. 1 is a schematic view showing an orthodontic wire mounted to the teeth.

Among several embodiments of the present invention, the first embodiment representing all the features of the present invention will be described with reference to the accompanying drawings. Regarding the second through fourth embodiments, they will be described with regard only to the elements different from those of the first embodiments. The same elements in the configurations of each embodiment shall be assigned the same reference numerals.

FIG. 1 schematically illustrates an orthodontic wire W coupled to the teeth, in order to allow the front teeth T to be directed toward the molars M and M', as the front teeth T are projected. To the orthodontic wire W are coupled a plurality of brackets B corresponding to each tooth, and the orthodontic wire W is supported by a wire supporting anchor A implanted around the molars M and M'. The wire supporting anchor A is implanted by means of the anchor implanting device of the present invention to be described later.

Figure 2:
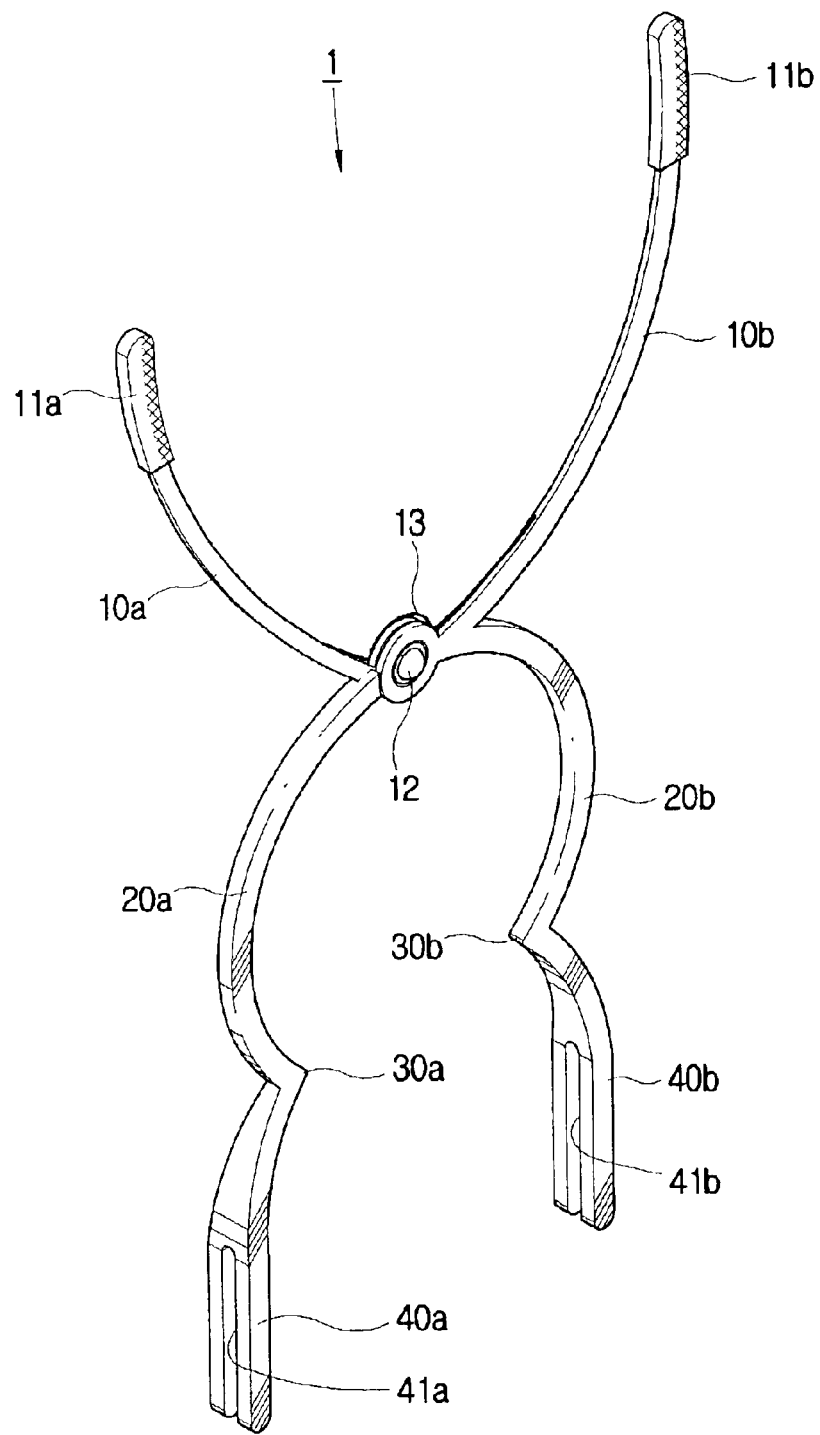
FIG. 2 is a perspective view of the an anchor implanting device according to a first embodiment of the present invention.

The anchor implanting device 1 according to the first embodiment of the present invention is, as shown in FIG. 2, comprised of tooth supporters 20a and 20b and handle parts 10a and 10b, which are connected by a shaft 12, a pair of locating projections 30a and 30b formed in the tooth supporters 20a and 20b, and anchor positioning units 40a and 40b connected to the tooth supporters 20a and 20b, establishing an implanting position of the anchor.

The handle parts 10a and 10b have respectively holding end parts 11a and 11b. An operator is allowed to hold them with two fingers to make the handle parts 10a and 10b approach to each other. To the handle parts 10a and 10b are coupled to the tooth supporters 20a and 20b, placing the shaft 12 in the middle thereof. The tooth supporters 20a and 20b may be formed integrally with the handle parts 10a and 10b, or separately formed and then coupled to the handle parts 10a and 10b.

To the shaft 12 is mounted an elastic spring 13, elastically biasing the tooth supporters 20a and 20b in a direction approaching each other, where the handle parts 10a and 10b approach to each other.

If the operator holds the holding end parts 11a and 11b and presses them to move the handle parts 10a and 10b toward each other, the tooth supporters 20a and 20b are spread out distantly from each other, relative to the shaft 12. However, if the operator removes the pressing force applied to the holding end parts 11a and 11b, the tooth supporters 20a and 20b become approaching to each other.

The tooth supporters 20a and 20b are placed in the center of a pair of neighboring molars M and M' to support partially the pair of neighboring molars M and M', along the transverse direction relative to the arrayed direction of the molars M and M'. Accordingly, it is preferable that the tooth supporters 20a and 20b are partially arced so as to partially contact and support the pair of molars M and M'.

Figure 3:
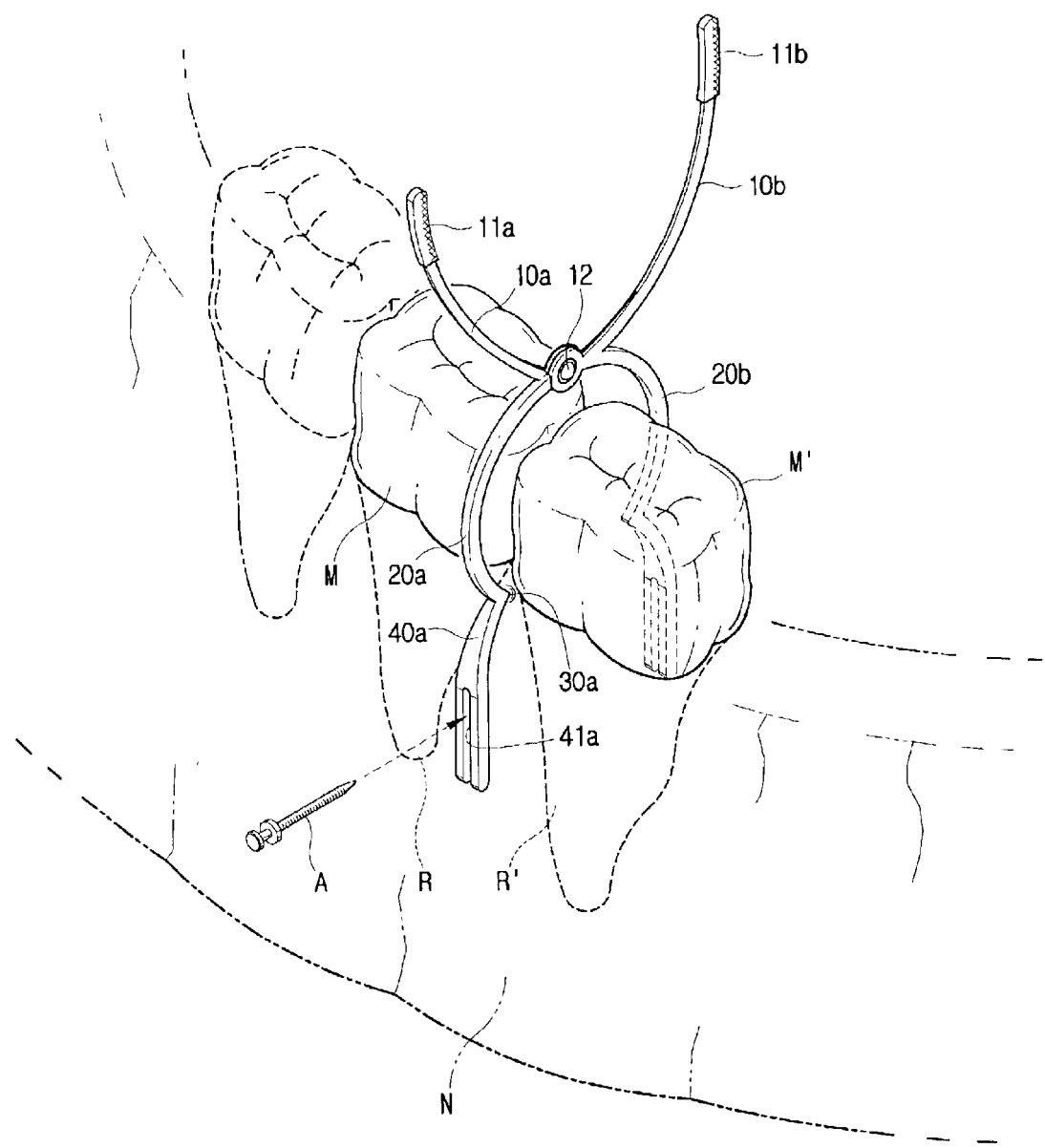
FIG. 3 is a perspective view showing the anchor implanting device coupled to the teeth.

From the respective tooth supporters 20a and 20b are extended the anchor positioning units 40a and 40b. The anchor positioning units 40a and 40b are, as illustrated in FIG. 3, placed on the sides of the gum, thereby establishing the implanting position of the wire supporting anchor A.

The anchor positioning units 40a and 40b are formed with anchor inserting grooves 41a and as long as predetermined, taking the shape of a fork. The anchor positioning units 40a and 40b are to some degree thick so as to guide the wire supporting anchor A vertically when implanting the wire supporting anchor A. The anchor inserting grooves 41a and 41b guide the wire supporting anchor A to the position on which it is implanted. At this time, to establish an exact implanting position of the wire supporting anchor A, it is more effective for the anchor positioning units 40a and 40b to be formed with a surface of curvature corresponding to the sides of the gum N.

The locating projections 30a and 30b are provided between the tooth supporters 20a and 20b and the anchor positioning units 40a and 40b, the locating projections 30a and 30b being projected inward in the radial direction and placed between the pair of molars M and M' and the gum N. The locating projections 30a and 30b serve to locate positions of the anchor positioning units 40a and 40b prior to implantation of the wire supporting anchor A.

A process of implanting the wire supporting anchor A with the use of the anchor implanting device 1 according to the first embodiment of the present invention will be described below.

The operator first holds the holding end parts 11a and 11b, and presses them so as to have the handle parts 10a and 10b approach to each other. Then, the tooth supporters 20a and 20b are spread so as to be distant from each other relative to the shaft 12. The tooth supporters 20a and 20b are positioned along the transverse direction to the arrayed direction of the pair of molars M and M', while partially enclosing and supporting the pair of molars M and M'. Then, if the pressing force applied to the holing end parts 11a and 11b is removed, the tooth supporters 20a and 20b become approaching to each other by the elastic spring 13.

Figure 4:
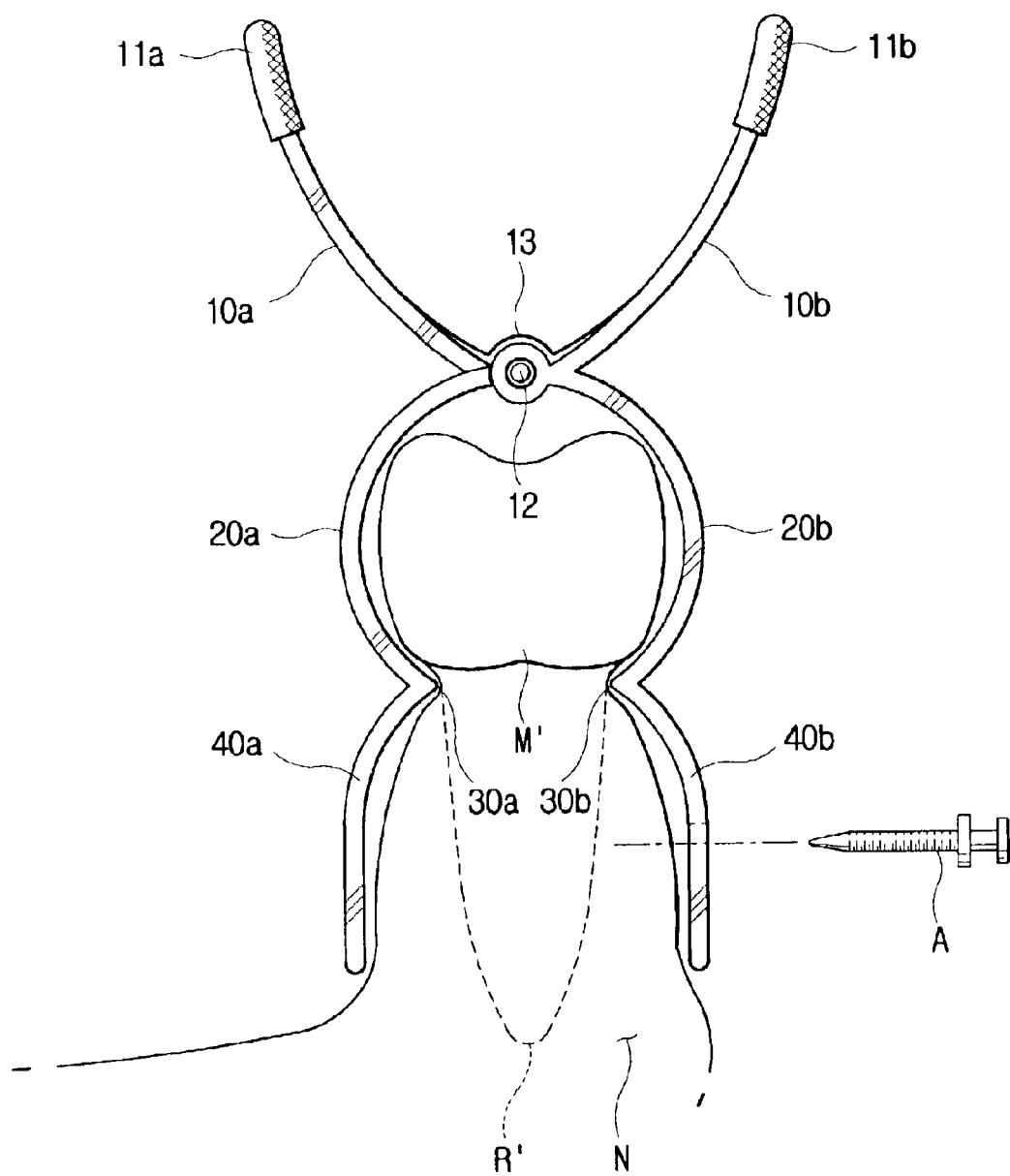
FIG. 4 is an enlarged side view of the main element of FIG. 3.

As illustrated in FIGS. 3 and 4, the anchor locating projections 30a and 30b are located between the pair of molars M and M' and the gum N, and in this connection, the anchor positioning units 40a and 40b can be positioned on the sides of the gum. If the anchor positioning units 40a and 40b are positioned on the sides of the gum N, the anchor inserting grooves 41a and 41b formed on the anchor positioning units 40a and 40b may be placed between the roots R and R' of the pair of molars M and M'.

Thereafter, the operator inserts the wire supporting anchor A through the anchor inserting grooves 41a and 41b and implants it to the gum N between the roots R and R' of the pair of molars M and M'. In this way, the operator can easily know the implanting position of the wire supporting anchor, thereby making it to operate the implantation in a simplified manner and reducing the time for operation of the implantation.

In the above-described first embodiment, there have been provided the handle parts 10a and 10b which the operator can hold. However, even though the handle parts 10a and 10b are not provided, there is no problem to accomplish the objects of the present invention.

Figure 5:
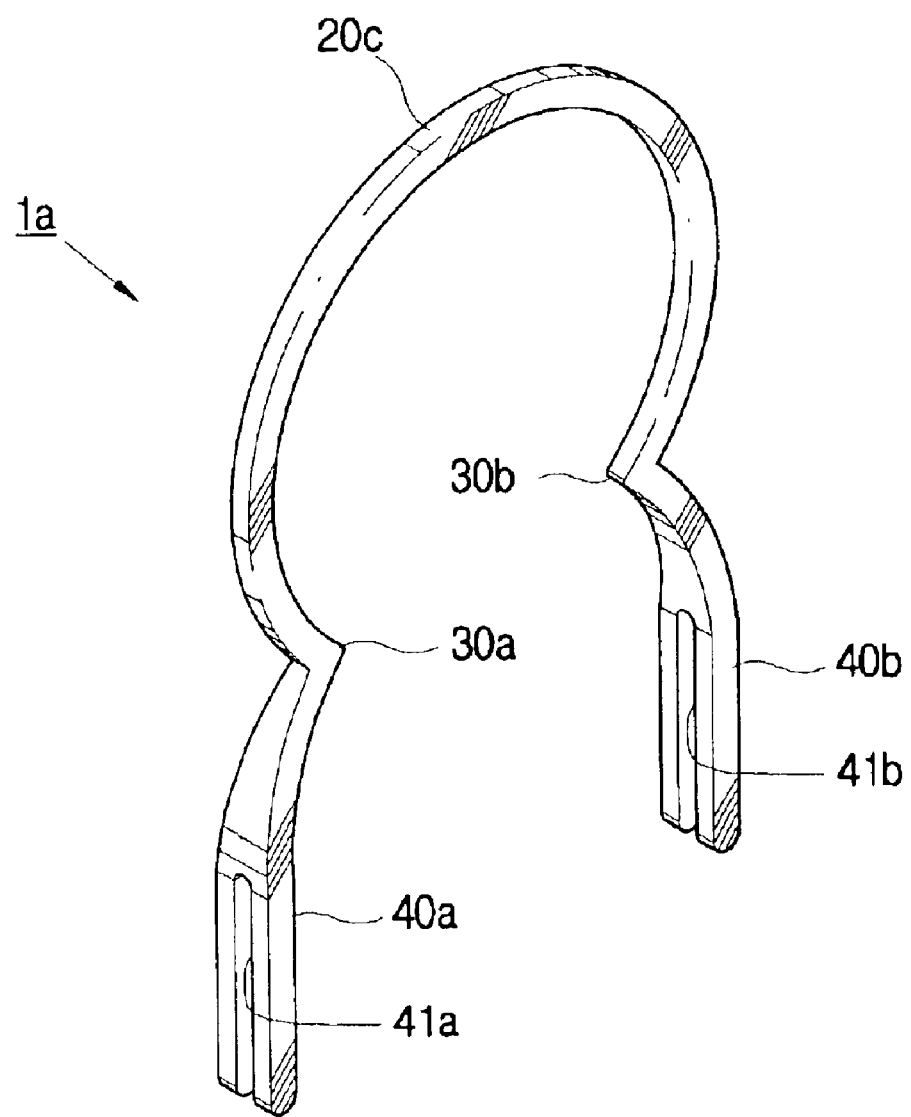
FIG. 5 is a perspective view of the anchor implanting device according to a second embodiment of the present invention.
Figure 6:
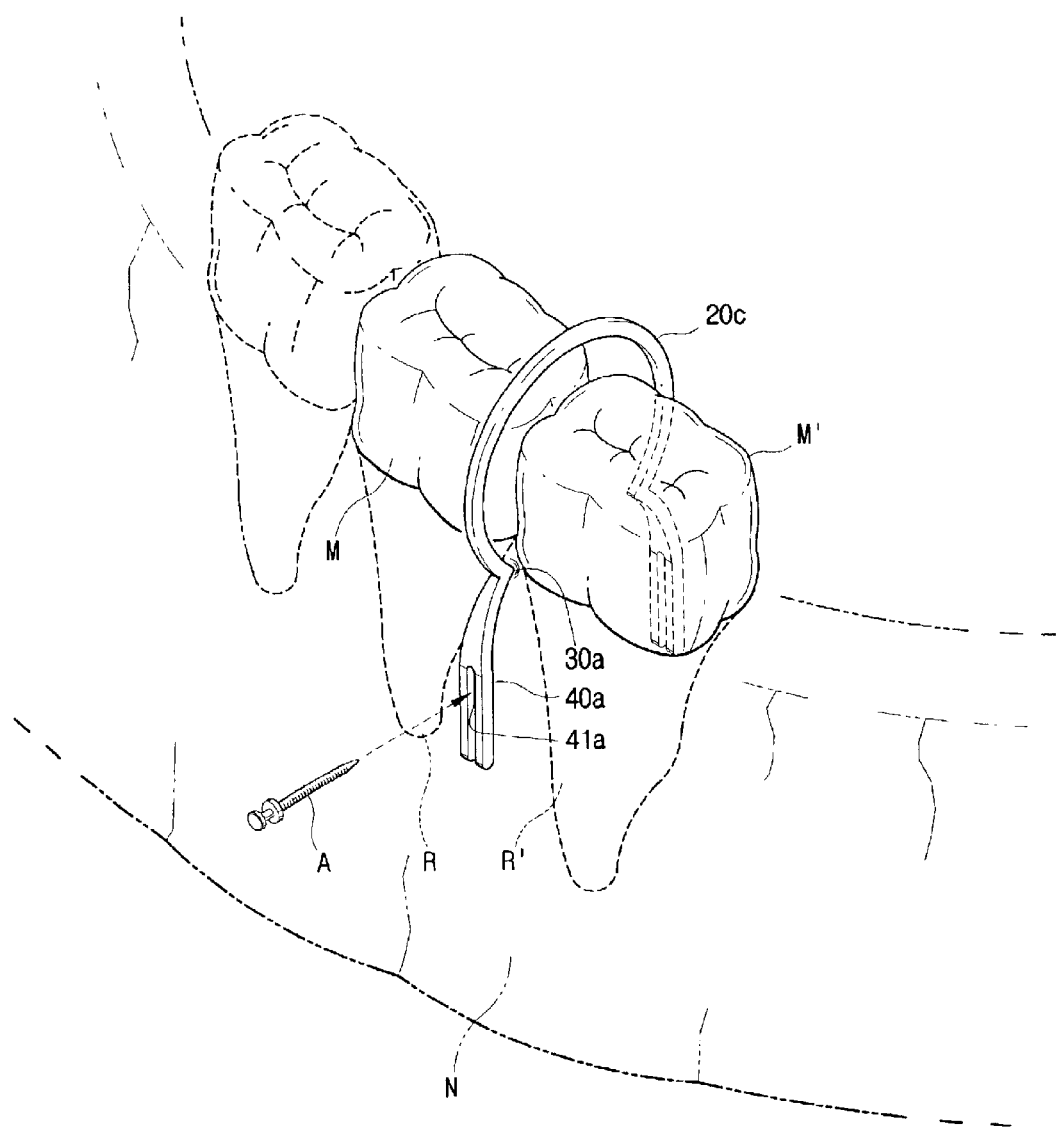
FIG. 6 is a perspective view showing the anchor implanting device coupled to the teeth, shown in FIG. 5.

To specify, the anchor implanting device 1a according to the second embodiment of the present invention can, as shown in FIGS. 5 and 6, be comprised of a tooth supporter 20c partially arced, both ends of which elastically approach toward between the pair of molars M and M', partially enclosing and supporting the pair of neighboring molars M and M' along the transverse direction relative to the arrayed direction of the molars M and M', the pair of locating projections 30a and 30b located between the pair of neighboring molars M and M' and the gum N, being projected inward in the radial direction of the tooth supporter 20c, and an anchor positioning units 40a and 40b connected to the tooth supporter 20c and positioned on the side of the gum, establishing an implanting position of the wire supporting anchor A.

The tooth supporter 20c is preferably manufactured with an elastic material such as a flat spring, so as to be elastically expanded and contracted.

Where the anchor implanting device 1a according to the second embodiment is used, the operator pulls out both end parts of the tooth supporter 20c so as to position the tooth supporter 20c between the molars M and M'. After the pair of locating projections 30a and 30b are located on the position between the molars M and M' and the gum N, the operator removes the pressing force applied to the tooth supporter 20c. Than, the tooth supporter 20c elastically expandable and contractible is contracted inward in the radial direction, and accordingly, the pair of locating projections 30a and 30b are located between the molars M and M' and the gum N. The anchor positioning units 40a and 40b may be positioned on the sides of the gum N, as in the first embodiment described above.

The operator can implant the wire supporting anchor A on the gum between the pair of molars M and M' and the gum N, positioning it through the anchor inserting grooves 41a and 41b formed in the anchor positioning units 40a and 40b. Thus, the operator can very simply perform the implanting operation of the wire supporting anchor A.

Figure 7:
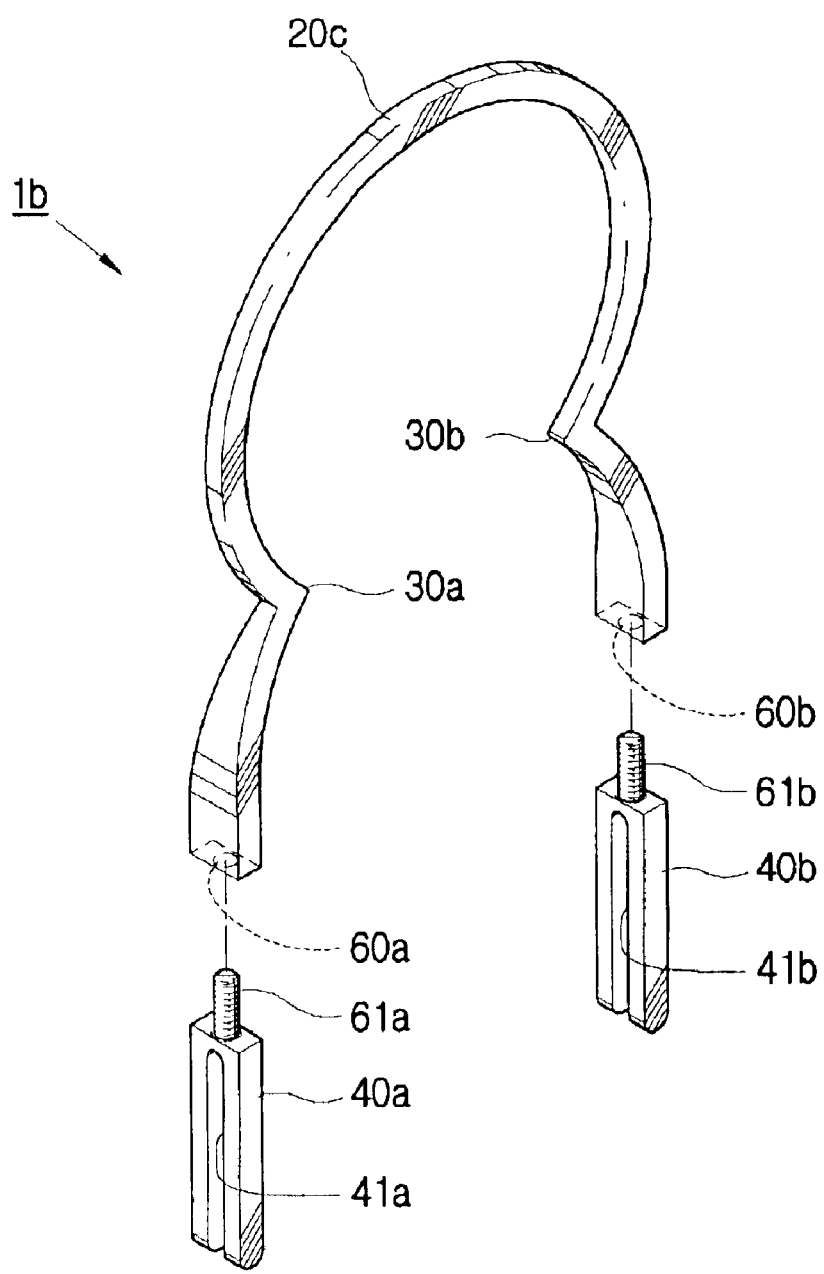
FIG. 7 is a perspective view of the anchor implanting device according to a third embodiment of the present invention.

The anchor implanting device 1b according to the third embodiment of the present invention is shown in FIG. 7. The anchor implanting device 1b according to the third embodiment is constructed so as to allow the anchor positioning units 40a and 40b to be detachably connected to the tooth supporter 20c, differently from the anchor implanting device 1a according to the second embodiment.

For this purpose, the anchor positioning units 40a and 40b are formed with male screwing parts 61a and 61b, and female screwing parts 60a and 60b are formed on both ends of the tooth supporter 20c. Accordingly, the length of the anchor positioning units 40a and 40b can be controlled relative to the tooth supporter 20c.

Figure 8:
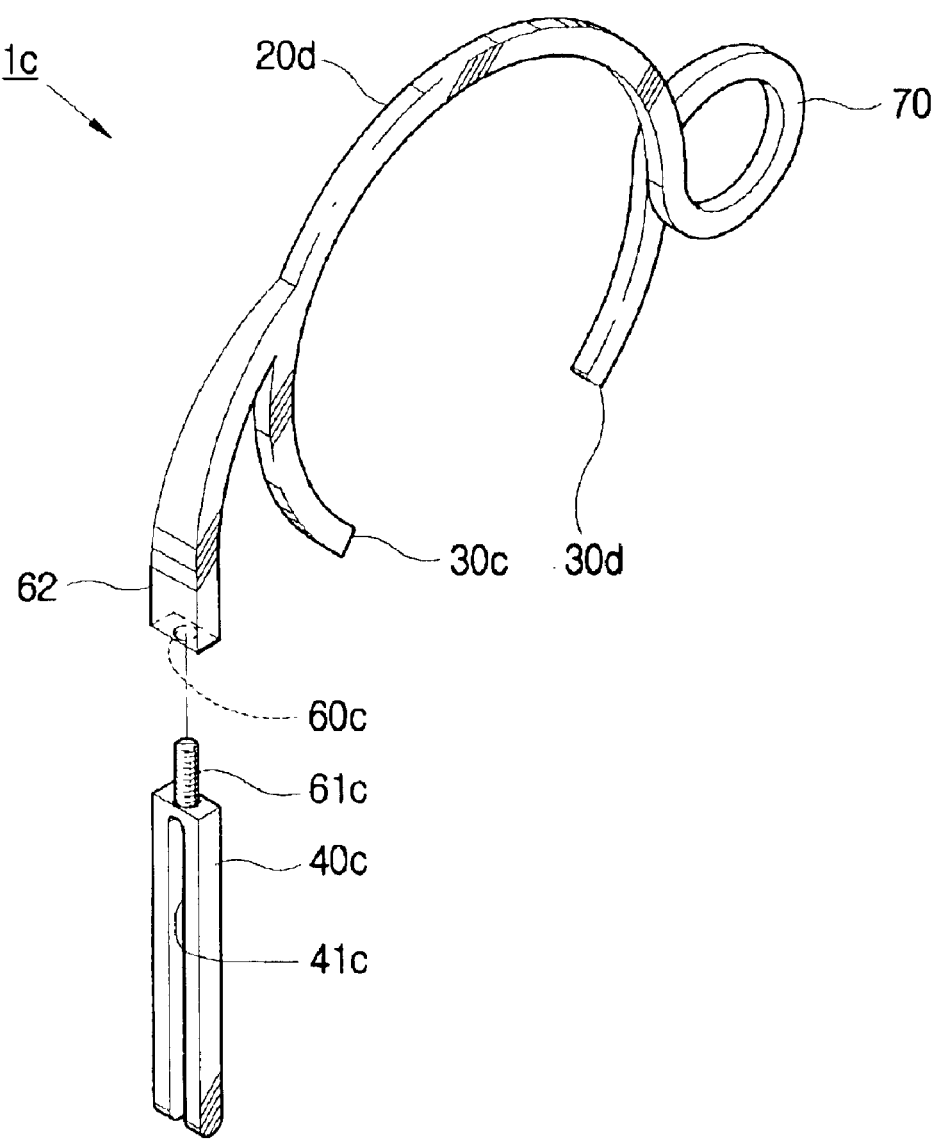
FIG. 8 is a perspective view of the anchor implanting device according to a fourth embodiment of the present invention.

The anchor implanting devices 1, 1a and 1b according to the first, second and third embodiments are respectively constructed with anchor positioning units in a pair. However, if there is no need to implant the wire supporting anchor A on both sides of the gum N, as depicted in FIG. 8 illustrating an anchor implanting device 1c according to the fourth embodiment, an anchor position unit 40c singularly can be provided in the tooth supporter 20d of the anchor implanting device 1c.

A dummy member 62 is separately provided in the tooth supporter 20d which has a female screwing part 60c, and it is of course detachable to the single anchor positioning unit 40c having a male screwing part 61c and a single groove 41c. A pair of locating projections 30c and 30d may become both free ends of the tooth supporter 20d, and the tooth supporter 20d can be used as a handling part 70 by bending a part thereof. The process of operating an implantation with the use of this device is the same as in the first through third embodiments, and thus, description thereof is deleted.

According to the present invention, there are provided four anchor implanting devices 1, 1a, 1b and 1c, for implantation of the wire supporting anchor A, thereby making the operation of implanting the wire supporting anchor A very easy. In addition, the time for operation has been much reduced, thereby providing the effect of cost saving accordingly.

In the above embodiments, it has been described that the wire supporting anchor is implanted around the molars. However, they can also be implanted around front teeth, and for this purpose, the anchor implanting device of the present invention can be used of course.

The wire supporting anchor may be independently implanted on the alveolar bone, then being connected with a variety of elastic units for orthodontics.

As described above, according to the present invention, there is provided an anchor implanting device for orthodontics, allowing a wire supporting anchor to be implanted on the predetermined position of the gum in an easy manner.

Further, by using the anchor implanting device according to the present invention, the time for operating the implantation of the wire supporting anchor is reduced, thereby accomplishing the effect of cost saving.

Although a embodiment of the present invention has been shown and described, it will be appreciated by those skilled in the art that changes may be made in these embodiments without departing from the principles and spirit of the invention, the scope of which is defined in the appended claims and their equivalents.

What is claimed is:

1. An anchor implanting device for orthodontics used for implanting
a wire supporting anchor, comprising:
a tooth supporter enclosing a volume portion elastically;
a locating projection projected inward in a radial direction from the tooth supporter; and
at least one anchor positioning unit extended from the tooth supporter, the anchor positioning unit taking the form of a fork and being formed with an anchor inserting groove;
whereby, when adjacent facing portions of neighboring teeth are enclosed by the tooth supporter and the locating projection is positioned on a side of a gum of the neighboring teeth, an implanting position of the wire supporting anchor is established.

2. The anchor implanting device according to claim 1, wherein the anchor positioning unit has a surface of curvature.

3. The anchor implanting device according to claim 1, further comprising a shaft rotatably supporting the tooth supporters in a pair, and wherein the anchor positioning unit is connected to each of the tooth supporters in a pair.

4. The anchor implanting device according to claim 3, further comprising a pair of handle parts respectively connected to the pair of tooth supporters, allowing the tooth supporters to approach to and separate from each other relative to the shaft.

5. The anchor implanting device according to claim 4, wherein an elastic spring is mounted on the shaft, elastically moving the pair of tooth supporters to be close to each other.

* * * * *